United States Patent
Cook et al.

(10) Patent No.: US 7,163,709 B2
(45) Date of Patent: Jan. 16, 2007

(54) COMPOSITION FOR DISINFECTION OF PLANTS, ANIMALS, HUMANS, BYPRODUCTS OF PLANTS AND ANIMALS AND ARTICLES INFECTED WITH PATHOGENS AND METHOD OF PRODUCING AND APPLICATION OF SAME

(76) Inventors: Robert Cook, 710 Rio Mar Dr., Vero Beach, FL (US) 32963; John Wayne Kennedy, 2219 Dairy Farm Rd., Gambrills, MD (US) 21054

(*) Notice: Subject to any disclaimer, the term of this patent is extended or adjusted under 35 U.S.C. 154(b) by 756 days.

(21) Appl. No.: 10/027,692

(22) Filed: Dec. 20, 2001

(65) Prior Publication Data

US 2003/0118705 A1  Jun. 26, 2003

(51) Int. Cl.
*A23L 3/34* (2006.01)

(52) U.S. Cl. ............... 426/322; 426/321; 426/335; 426/532

(58) Field of Classification Search ........ 426/321, 426/322, 335, 532, 541
See application file for complete search history.

(56) References Cited

U.S. PATENT DOCUMENTS

| | | | |
|---|---|---|---|
| 1,620,490 A | | 3/1927 | Sanders |
| 2,655,460 A | | 10/1953 | Kise ............... 167/22 |
| 3,959,255 A | | 5/1976 | Chazan et al. ........ 260/210 |
| 3,981,861 A | | 9/1976 | Chazan et al. ........ 536/17 |
| 4,064,339 A | | 12/1977 | Coussediere et al. .... 536/17 |
| 4,098,602 A | | 7/1978 | Seymour et al. ....... 71/67 |
| 4,906,466 A | * | 3/1990 | Edwards et al. ...... 424/421 |
| 4,952,398 A | * | 8/1990 | Tapin ............... 504/121 |
| 5,560,821 A | * | 10/1996 | Leo et al. ........... 210/143 |
| 5,665,679 A | * | 9/1997 | McInnes ............. 504/164 |
| 5,753,493 A | | 5/1998 | Wiersma ............. 435/261 |
| 5,780,064 A | | 7/1998 | Meisters et al. ...... 424/616 |
| 6,015,816 A | * | 1/2000 | Kostyniak et al. ..... 514/299 |
| 6,022,545 A | | 2/2000 | Schmittmann et al. .. 424/195.1 |
| 6,093,414 A | * | 7/2000 | Capelli ............. 424/405 |
| 6,277,416 B1 | | 8/2001 | Harkrader et al. ..... 424/725 |
| 6,294,186 B1 | * | 9/2001 | Beerse et al. ........ 424/405 |
| 6,346,281 B1 | * | 2/2002 | DeAth et al. ........ 424/725 |
| 6,365,130 B1 | * | 4/2002 | Barry et al. ........ 424/48 |
| 7,060,302 B1 | * | 6/2006 | Hickok ............. 424/617 |

* cited by examiner

*Primary Examiner*—Leslie Wong
(74) *Attorney, Agent, or Firm*—Jack Schwartz & Associates

(57) ABSTRACT

The present invention discloses a composition and method of providing ionic forms or compounds of any combination of three metals to produce a product that can be used as a antimicrobial as defined by the U.S. Environmental Protection Agency (EPA) such as a hard surface disinfectant and as a foliar spray or water treatment for the control of various diseases in garden row, field and tree crops, on hard surface areas such as equipment from infected fields or in hospitals, homes, etc. as well as against a wide range of human, plant and animal diseases. Additionally, the composition of the present invention is able to be used to coat and otherwise treat and disinfect food products such as but not limited to fish and shellfish, meat, milk, poultry, eggs and irrigated crops (both food and nonfood crops) as well as non food products as defined in the EPA exemption from tolerance for copper and copper products. The composition may include inerts such as surfactants, detergents and buffers to adjust the pH. The composition remains soluble in water and is useful efficacious against the spread of bacteria, viruses and fungi and other pathogens within a source of water such as a reservoir or pool. Alternatively, the composition may be in aerosolized, misted, vaporized, fogged, humidified forms to produce micronized particles which are able to remain in suspension in the air for long periods of time in order to act on air-borne fungal spores and/or pathogens.

10 Claims, No Drawings

COMPOSITION FOR DISINFECTION OF PLANTS, ANIMALS, HUMANS, BYPRODUCTS OF PLANTS AND ANIMALS AND ARTICLES INFECTED WITH PATHOGENS AND METHOD OF PRODUCING AND APPLICATION OF SAME

BACKGROUND OF THE INVENTION

1. Field of the Invention

The present invention is related to fungicides, including but not limited to bacteriacides, and more particularly to new techniques for disinfection of plants, animals, humans, by products of plants and animals and articles infected with pathogens using unique formulations and methods of application of ionic copper and copper compounds including copper sulfate pentahydrate and other copper salts alone or ionic silver alone and silver compounds including silver sulfate and other silver salts alone and ionic gold alone and gold compounds including gold sulfate and other gold salts alone and combinations of ionic copper, ionic silver and ionic gold and copper, silver and gold compounds. The above invention is used with or without inert ingredients such as surfactants and/or detergents to enhance the efficiency of the invention.

2. Background of the Invention

Plant and animal diseases, including but not limited to viruses, bacteria, fungi and other pathogens have plagued mankind for centuries. There are several mechanical, chemical and biological tools and methods of application of these tools that manage diseases, but most have major draw-backs that limit use of the technology.

Many kinds of substances have a deleterious effect on microorganisms. Antimicrobial substances have two kinds of activity, the first being bacterial, germicidal or virucidal and effective against other organisms such as slime, molds, etc. and other microorganisms; and the other being bacteriostatic, fungicidal, or growth-inhibiting. Antimicrobial activity is a property of both inorganic and organic substances, and the exploitation of such activity is a matter of considerable practical importance in the development of antiseptics, sanitizers, germicides, bactericides, sporicides, virucides, disinfectants and others.

A number of inorganic substances have antimicrobial activity because of the toxicity to the ions into which they dissociate or because of their activity as oxidizing agents which brings about some degree of oxidation of cell substance. Among the inorganic substances which act as antimicrobial agents are salts and other radicals attached to metals. The degrees to which salts are effective as toxic agents are mainly dependent upon the degree of dissociation of the salt and other radicals, the nature of the anion, and the valence and molecular weight of the metallic ion. In general, the bivalent cations, which are more toxic than the monovalent cations, and the salts and other radicals including oxides of the heavier metals are more toxic than those of the lighter metals. The antimicrobial activity of the heavy metal salts and other radicals are attributed to the affinity of the cations for protein material. When the constituent protein of the bacterial cell is precipitated as an insoluble proteinate, the cell dies. However, other factors may also be involved that are not totally understood and are being investigated. The free ions of the metals copper, silver and gold give positive results when used alone. Additionally, experiments demonstrate a synergy between the ions of these metals when used in combinations. Greater efficacy is achieved through the use of surfactants and/or detergents and other additives such as buffers to adjust the pH of the finished formulation and/or ionic properties of the product.

The processes of effecting bacterial growth-inhibition or death are subject to a variety of influences. The most important of these influences is the concentration of the reacting substances, i.e., concentration of the biocidal substance and the numbers of bacteria present. The effective concentration of a biocidal substance is, in turn, dependent upon primarily two other factors: first, the presence of moisture, which makes possible ionization of the substance to form the biocidal agent and acts as a suspending medium in which there may be intimate contact between the biocidal agent and the microorganism. Second, the presence of extraneous organic and/or other matter which will react with the agent prior to contact with an organism thereby rendering the agent ineffective.

It has been established in antimicrobial activities that salts and other radicals of heavy metals are rapidly precipitated by extraneous organic or other material and, therefore, while such salts may have an initial cell kill at an initial effective concentration, the effective concentration is rather quickly reduced by combination of the metal with such extraneous matter, thereby depleting the amount of toxic metal available for biocidal activity. Therefore, while the radicals offer, in certain instances, the property of aqueous solubility and, therefore, allow for the dissociation and availability as toxic metal agents, they may be rendered ineffective rather quickly such that prolonged or controlled destruction or inhibition of bacterial action is unavailable. On the other hand, metal radicals or complexes of organic moieties such as organic acids or the like possess a degree of dissociation which is normally not as great in comparison to, for example, highly soluble inorganic salts. Therefore, whereas the metal complexes have a greater stability or kinetic inertness with respect to extraneous organic matter present in the environment of living cells, there is also generally a loss of toxic effect by reason of their higher stability.

Superimposed on this brief background discussion of antimicrobial activity is the relation of fungus, including bacteria growth to the acidity or alkalinity of the media conducive to such growth.

Concentrations of hydrogen ions compatible with growth are very low, generally, on the order of about $10^4$ to $10^9$ moles of hydrogen ions per liter. As an example, almost all bacteria will grow at about pH 7.0 ($1 \times 10^7$ moles hydrogen ion per liter) but thrive best at optimum pH's which vary from species to species. The minimum and maximum limits between which viability is possible likewise vary widely with species. The activity, therefore, of an antimicrobial agent in the pH range of microbial viability is a very important consideration in that the activity determines biocidal efficacy. The target organism can be determined to be in a certain pH range and the formulation adjusted. Inert ingredients such as surfactants and detergents act on the walls or structure of resting spores, for example, or other dormant stages of fungi, including but not limited to bacteria, viruses, fungus to weaken the protective capsule surrounding the otherwise stages of the fungi to the invention.

In substance, heretofore in the prior art there appear to have been two extremes made available by antimicrobial metallic compositions. On the one hand, known metal compounds have a high degree of dissociation such that metal ions are quickly and copiously made available by virtue of rapid dissociation with formation of ionized species. These species react so as to saturate all available ligands and are thereby rendered inactivated as to cidal potential in a very narrow time frame, with little residual killing power. Thus, they are rendered relatively ineffective as biocidal agents over prolonged periods of time. Other known metal compounds are relatively stable and provide minimal amounts of ionized species over the normal physiological pH range, providing, therefore, minimal growth inhibitory or toxic potential, due to the very minimal degree of dissociation inherent in them.

Metal salts or metal complexes have been used as antimicrobial agents. Representative of prior art patents directed to the use of metal salts or metal chelates of inorganic or organic compounds as microbiocidal agents include: U.S. Pat. Nos. 871,392; 991,261; 1,620,490; 1,679,919; 1,785,472; 2,208,253; 2,269,891; 2,456,727; 2,494,941; 2,655,460; 2,878,155; 2,900,303; 2,901,393; 2,938,828; 3,076,834; 3,099,521; 3,206,398; 3,240,701; 3,262,846; 3,266,913; 3,681,492; 3,782,471; 4,098,602; and 4,952,398.

Of these above listed prior art references, the four (4) most relevant are now to be discussed and distinguished in greater detail. First, U.S. Pat. No. 1,620,490 teaches a composition formed by placing Quick Lime in a mixer or hydrator. The lime is caused to hydrate while copper sulfate is added and a dust is produced. This patent simply discloses that silver may be used in place of copper. This patent neither discloses nor suggests the use of silver, copper and/or gold either alone or in combination as in the present invention.

Next, U.S. Pat. No. 2,655,460 discloses a fungicidal composition containing silver. This composition contains diluted dibasic silver salts which are dried and powered. This patent also discloses the use of copper as a fungicide. This patent neither discloses nor suggests the combination of silver, copper and/or gold. This reference also neither discloses nor suggests the use of silver, copper and/or gold either alone or in combination as in the presently disclosed invention.

Thirdly, U.S. Pat. No. 4,098,602 discloses a composition effective against the growth of algae. The composition includes a combination of an ammonium quaternary compound and a copper complex. This patent neither discloses nor suggests a composition containing both silver, copper and/or gold. Similarly to the previously mentioned U.S. Patents this patent also neither discloses nor suggests the use of silver, copper and/or gold either alone or in combination as in the instant invention. As this patent also neither discloses nor suggests the main inventive features of the instant invention, it is submitted that the present invention is patently distinct over this reference.

Finally, U.S. Pat. No. 4,952,398 discloses a biocidal composition containing copper. The composition is used as a treatment for water by providing increased biocidal activity. The composition is also effective for disinfecting animal breeding places and the cleansing of soil. The composition combines a quaternary ammonium compound with copper salt. This patent neither discloses nor suggests a composition containing silver, copper and/or gold either alone or in combination for the purposes set forth in the present invention. While these units may be suitable for the particular purpose to which they address, they would not be as suitable for the purposes of the present invention as heretofore described.

SUMMARY OF THE PRESENT INVENTION

The present invention discloses a composition and method of providing ionic forms and/or compounds of any combination of three metals to produce a product that can be used as a hard surface disinfectant and other antimicrobial uses, such as those defined by the U.S. Environmental Protection Agency, and as a foliar spray for the control of various diseases in garden row, field and tree crops, on hard surface areas such as equipment into or exiting infected fields or in hospitals, homes, etc. as well as against a wide range of human, plant and animal diseases. Additionally, the composition of the present invention is able to be used to disinfect food products such as but not limited to fish and shellfish, meat, milk, poultry, eggs and irrigated crops (both food and nonfood crops) as well as water and other non-food products. The composition remains soluble in water and certain other liquids and is efficacious against the spread of bacteria, viruses and fungi within a source of water such as a reservoir or pool, for example. Alternatively, the composition may be used in aerosolized, misted, vaporized, fogged, humidified, etc. forms to produce micronized particles which are able to remain in suspension in the air for long periods of time in order to act on air-borne fungal, bacterial, viral, and other spores and/or forms of pathogens.

The composition is formed from combinations of ionic copper, silver and/or gold and copper, silver and/or gold compounds. The composition is efficacious against a wide variety of viruses, bacteria and fungus and other pathogens which cause numerous diseases in plants, animals and humans. Furthermore, the composition is able to effectively disinfect plants, animals, humans, products of plants, animals and humans and articles infected with pathogens.

Ionic copper, ionic silver and ionic gold alone and in any combination thereof as well as copper, silver and gold compounds alone and in any combination thereof as in the composition of the present invention have demonstrated efficacy against a wide range of plant and animal diseases. The composition of the present invention providing inventive and efficacious combinations of ionic copper, ionic silver and ionic gold alone and copper, silver and gold compounds as well as expanding on the uses and methods of application beyond any uses previously contemplated. Studies performed by the inventors involving the composition of the present invention suggest a very wide scale of applications given the proper formulations and methods of application. The use of inerts such as surfactants, detergents, buffers to adjust pH and that stabilize the ionic condition will improve the efficacy of the invention.

The composition of the present invention creates an agent composed of copper and/or silver and/or gold that for example eradicates *Xanthomonas citri*, better known as citrus canker. Citrus canker is now most prevalent in Florida, as well as other places worldwide. Our example has shown that a close relative accepted by APHIS, USDA (*Xanthomonas axononodis*) was considered an "eradicate" in closely monitored studies.

A significant problem existing at the present time is the general paranoia regarding Anthrax and botulinum. Anthrax and botulinum are bacteria, as is Xanthomonas. Studies conducted by the inventors of the composition demonstrate the efficacy of copper sulfate pentahydrate, such as a solution produced by the Magna Bon Corporation, and this compound plus a silver compound against citrus canker, a serious plant disease of citrus that is caused by a bacteria in the Genus Xanthomonas. The studies conducted on citrus canker achieved a quicker level of control at a level considered an eradicant than any other of the antimicrobials tested. Anthrax is caused by a bacterium in the Genus Bacillus. Based upon the results obtained in studies conducted on citrus canker, it follows that the composition of the present invention including copper sulfate pentahydrate, or a combination of a silver compound with copper sulfate pentahydrate or a combination of a gold compound with copper sulfate pentahydrate is effective against Anthrax. The composition of the present invention includes all combinations of ionized copper, silver and gold as well as copper, silver and gold compounds. Inerts such as surfactants, detergents and buffers may be added in certain cases to improve efficacy.

The composition of the present invention is able to be produced in numerous forms such as an aerosolized, misted, vaporized, fogged, humidified forms to produce micronized particles which are able to remain in suspension in the air for long periods of time in order to act on air-borne fungal spores and/or other pathogens. The composition may also be suspended in solution for washing, coating and otherwise disinfecting food products such as but not limited to fish and shellfish, meat, milk, poultry, eggs and irrigated crops (both food and nonfood crops) as well as non food products. Additionally, the composition may be added to and remain in suspension within sources of liquid such as reservoirs and pools to disinfect and/or eradicate any pathogens within the source of liquid. The composition of the present invention is non-toxic to plants, animals and humans and thus ingestion of a food product which has been washed and/or otherwise treated with the composition, drinking a liquid containing the composition or bathing in a liquid containing the composition does not cause any adverse side effects. Additionally, the composition of the present invention may be formulated in liquid form, formulated into soaps or salves or other forms which may be used on skin or applied to an area affected by a pathogen.

The copper sulfate pentahydrate formulation has been used as an effective algaecide, bactericide and fungicide for many years. Millions of pounds of copper are sprayed yearly for various diseases such as melanose, scab, alternaria and other crop harming diseases.

It is known that the copper must be in a bioactive form for it to work effectively. Metallic copper is nearly inert. However, it is somewhat water soluble and minute amounts of ionic copper, as little as 1 ppm is enough to treat the diseases mentioned. Copper has been used in container construction of water vessels as early as the Roman era for that purpose, but not enough available copper ions are present to significantly lower the reproduction of pathogens.

Most of the copper used is in powder form, bulky, dusty, heavy an hard to handle. There are also copper products formulated as liquids such as copper hydroxide. In sum, bioactive copper is used extensively, worldwide for certain applications. The compositions of the present invention expand on the uses of copper in ionic form as well as copper compounds used alone as well as in combination with ionic silver, silver compounds, ionic gold and gold compounds to uses never before contemplated. The ionic silver, silver compounds, ionic gold and gold compounds each produce an efficacious composition when used alone or in any combination with the above metals.

Review of the literature directed the inventors of the present invention to explore new approaches. When the inventors of the composition of the present invention chemically combined silver with copper, a synergistic effect was produced, and the resulting compound becomes a far more powerful disease killer than existing copper based products. This fact was borne when two products made with the herein disclosed composition were tested against Citrus Canker in a study entitled "A SCREENING EVALUATION OF ONE PRODUCT FOR ITS ANTIBACTERIAL PROPERTIES WHEN CHALLENGED WITH ONE MICROORGANISM STRAIN". This study was performed by Bio Science Labs, (See Protocol #000803,infra.).

Lot #1, which contained ionic copper, diluted to a concentration of 15 ppm copper, killed *Xanthomonas axonopodis* at the rate of 37% in one minute.

Lot #2, containing a 9:1 ratio of 15 ppm copper and 150 ppb of silver, killed 97% of the *Xanthomonas axonopodis* in one minute.

Clearly, the addition of silver to the composition enhanced the disease killing power of the copper composition. Experimentation by the present inventors indicate a ratio of 9:1 copper:silver as being ideal combination of metals. However, ratios from between 32:1 and 1:1 copper:silver may be used and effective for purposes of the present invention and dependent upon the intended use of the composition.

Protocol #00803

Preliminary Data

| Product and Lot # | Product Concentration (v/v) | Exposure Time[1] | Log 10 Reduction | Percent Reduction |
|---|---|---|---|---|
| Magna-Bon Pro-Teck Plus, 60 ppm copper with 600 ppb silver lot = #000216F | 99% | 1 minute | >5.9004 | 99.9999% |
| | | 5 minutes | >5.9004 | 99.9999% |
| | | 10 minutes | >5.9004 | 99.9999% |
| | | 30 minutes | >5.9004 | 99.9999% |
| | | 60 minutes | >5.9004 | 99.9999% |

In-Vitro Time-Kill Evaluation
Xanthomonas Axonopodis USDA #46190

| Product and Lot # | Minimum Inhibitory Concentration (MIC) (Product Dilution) |
|---|---|
| Magna-Bon Pro- Teck Plus, 60 ppm copper with 600 ppb silver lot #000216F | <1:4 |

Minimum Inhibitory Concentration (MIC) Evaluation
Xanthomonas axonopodis USDA #46190

It is therefore a primary object of the present invention is to provide a composition that will eradicate and/or control pathogens and be used as a fungicide, bacteriacide, germicide or virucide in killing microorganisms.

Another object of the present invention is to provide an enhanced antimicrobial composition and method for its production, that can be used to against a wide range of human, plant and animal diseases as well as minimize the growth and spread of diseases and slimicides, etc. in plants and plant surfaces.

An even further object of the present invention is to provide an enhanced antimicrobial composition and method for its production that can be used to purify water.

A yet further object of the present invention is to provide an antibacterial composition which can be used to disinfect and/or eradicate bacteria such as Anthrax, botulinum, *Xanthomonas citri,* better known as Citrus Canker as well as other fungi, bacterium and viruses.

A still further object is to provide a surface disinfectant for hospitals, homes and other areas that require hard surface disinfectants.

A still further object of the present invention is to provide an antibacterial composition which can be used as a bacteriostatic or growth inhibitor to microorganisms.

A still further object is to develop a product to be used on plants for disease control.

A yet further object of the present invention is to be combined with water supplies such as a reservoir or pool or bottle or otherwise container water for eliminating bacteria within a water supply.

A still further object of the present invention is to provide a composition able to remain in suspension for use in coating or otherwise treating food products such as but not limited to fish and shellfish, meat, milk, poultry, eggs and irrigated crops (both food and nonfood crops) as well as non food products to coat or otherwise treat the product and eliminate any bacteria on or within the food product thereby minimizing pathogens resulting from ingestion or inhalation of pathogens or dermal contact of the food product and coating the food product to increase the shelf life of the food product by elimination of pathogens and/or storage fungus.

A yet further object of the present invention is to provide a composition which is safe to man, animals, plants and articles infected with pathogens as well as safe for the environment.

An even further object of the present invention is to provide a composition which is easy to handle and store, has excellent storage stability and is not corrosive to machinery, etc. made of metal or plastic and other materials used in manufacturing, or other processes in commerce.

A yet further object of the present invention is to provide a composition able to be produced in at least one of an aerosolized, misted, vaporized, fogged, humidified forms to produce micronized particles which are able to remain in suspension in the air for long periods of time in order to act on and eradicate or disinfect air-borne fungal spores and/or other pathogens.

Another object of the present invention is to provide a composition that is simple and easy to use.

A still further object of the present invention is to provide a composition that is economical in cost to manufacture.

Additional objects of the present invention will appear as the description proceeds.

Other objects, advantages and novel features of the invention will become readily apparent to those skilled in the art from the following detailed description and examples of a preferred embodiment of the herein disclosed and claimed in the antimicrobial composition.

DETAILED DESCRIPTION OF THE INVENTION

The present invention discloses a combination of a copper, silver and gold in ionic form and compounds thereof and other radicals in combinations. When such combinations are combined in specific ratios, the combination is able to remain in a solution, wherein the solution remains in ionic form. Surfactants, detergents and/or buffering agents may be added to the composition to adjust the pH.

The inventors of the present invention petitioned and received an exemption from tolerance for copper sulfate pentahydrate from the U.S. Environmental Protection Agency (EPA) for food uses of the product on plants and animals. The exemption provides for a broad pattern of uses for disease control of plants and animals. Therefore the utility of the composition of the present invention will provide for use of the product in virtually all settings. However, other uses are disclosed herein for the composition of the present invention.

Anthrax, Botulinum, and other human and animal diseases (pathogens) have several modes of introduction into humans and animals, including dermal (through the skin, etc.), ingestion and inhalation.

Ingestion

The composition of the present invention is effective against pathogens in water and can be used at rates that are effective against Anthrax, Botulinum and other human and other animal pathogens. It is known that post harvest drenches of the product on fruits, vegetables, animal by-products, milk, eggs, poultry and other articles named in the exemption from tolerance will greatly reduce or eliminate pathogens. The compositions of the present invention are capable of eliminating the threat of Anthrax and Botulinum and other pathogens threatening humans and animals.

The product is also effective in reducing and/or eliminating pathogens that result during storage and handling of fish, shellfish, poultry, meat products of cattle, sheep, pigs and other animals. Rinsing, dipping and/or washing and other means of treatment of the animal products provides control and/or elimination of pathogens that affect humans and/or other animals. The compositions of the present invention are effective in controlling and/or eliminating pathogens such as Anthrax and/or Botulinum and other diseases or pathogens including protozoans, etc. of importance to human and animal health when used in a similar manner.

The composition is also effective in controlling and/or eliminating storage pathogens in liquids such as, but not limited to, water, juices, milk, etc. The composition, when used to wash and coat and other means of treatment food and non food products greatly extends the shelf life of these liquids by eliminating the storage diseases while not affecting the food and nonfood products.

In addition, several other uses for the composition include application to plants and/or animal by-products, water and milk and milk by-products, juices and other liquids used in man and animal diets. Such use patterns and formulations include use directly or indirectly on humans and/or other animals and/or plants.

Inhalation

The composition can be used in aerosolized, misted, vaporized, fogged, humidified or other forms used to produce micronized particles of the composition that can remain in suspension in the air for long periods of time. The micronized particles act much like a fumigant to provide total coverage to all sides of a surface that may be infected with pathogens. In any of these forms, the composition is able to intercept fungi (including bacteria, fungus, virus), spores and/or resting (dormant) stages of the pathogen in the air. The composition prompts the pathogen to vegetate and/or otherwise vitalize the dormant stage of the pathogen and the formulation as defined by itself or in combinations with other components of a formulation capable of killing the vegetative stage and/or spores and/or resting spores and/or resting stage of the pathogen by contact and/or action of the total formulation on the pathogen.

The formulation of the composition includes inert ingredients such as, but not limited to surfactants, detergents or semiochemicals that affect the dormant stage by acting on the cell walls or structure of the pathogen allowing the composition to kill the most resistant life stage of the pathogen. For example, the cell walls of bacteria and other fungal spore are hydrophilic (attract and absorb water). A micronized mist contains water and thus, is attracted to the structure of the fungus. The Bacillus wall is compromised by the use of surfactants, detergents and/or semiochemicals and the composition of the present invention is then able to kill the bacteria. If the bacteria spore or resting spores are coated, the material (such as a gelatin) used in the coating is usually hydrophilic. Again, the coating of the resting spore and/or the cell wall of the bacterium is compromised by the mist containing the formulation allowing the composition of the present invention to kill the bacterium.

In addition, certain compounds such as ethylene gas prompt vegetative stages such as seeds to germinate and such compounds can be added to the total formulation to force the resting stages of pathogens to vegetate. Semiochemicals such as growth enhancing products that induce germination may also be used in a custom made formulation for any particular use pattern against the target pathogen.

The micronized particle use pattern can be used in any situation where air-borne pathogenic fungal spores and/or other vegetative or reproductive stages of pathogens are present. The composition of the present invention is thus able to be used to eradicate highly refined Anthrax, Botulinum and other animal and plant air-borne pathogens.

Dermal

Many pathogens, including Anthrax, enter a body or organism through cuts and/or abrasions on the skin. The product and/or other products mentioned in this disclosure can be utilized in liquid form, formulated into soaps or in salves or other forms used on skin that can be applied to the affected area. The mode of action of the pathogen is the same as discussed above with respect to the other modes of action (ingestion and inhalation). Preliminary efficacy studies of the composition of the present invention indicate efficacy on cuts and abrasions using salves and liquid products. Theoretically, the pathogen is eliminated from the dermal abrasion or cut and a protective barrier aids in the protection of the wound. Again, inerts in the formulation aid in destroying the integrity of the dormant stage protective barrier.

Anthrax is most potent as a dermal substance when the dermis of the human or animal is compromised. The bacteria become established when the resting spore becomes active (vegetates). The bacteria then enter the body and are transported throughout the bloodstream. The systemic action in the vascular system can be prevented at a point of entry by use of the product and/or other product combinations.

Summary

Using the composition of the present invention, the threat of infection by pathogens such as Anthrax and/or Botulinum and other pathogens through routes into the human and/or animal systems by the dermal, ingestion and inhalation route of entry is greatly decreased. The composition of the present invention is able to be also used as a preventative measure to decrease the possibility of infection by pathogens. Plant pathogens are mitigated in the same manner.

Ingestion

Plant and animal products can be disinfected using the formulations previously discussed prior to ingestion by humans and/or animals. This includes treatment of post-harvest fruits and vegetables, treatment of animal by-products, fish and shellfish, etc. as defined in the exemption from tolerance. The treatment includes washing or soaking or other means of treatment of the food product in the liquid state in which the composition is suspended. Water and other liquids can also be treated to eliminate pathogens by addition of the composition thereto.

Inhalation

The formulation can be applied in micronized-sized particles that can intercept and mitigate air-borne particles of pathogens prior to the pathogen being inhaled. The cell walls of many pathogens such as Anthrax and Botulinum are hydrophilic and in any coating that is used to produce a "refined" product, the cells are most certainly hydrophilic. The aqueous formulation with or without additives act on cell walls and/or coatings thereby compromising the cell. Certain compounds such as surfactants and/or detergents can be added to aid the vegetation of resting spores or other stages of the pathogen. Once the cell is compromised, the composition of the present invention is able to act thereon causing death thereto. A reason Anthrax or other bacteria activates is that the spores hit the mucous membrane in the nose, throat, etc. and vegetate leading to spread throughout the body. By compromising the coating and/or cell wall, the composition of the present invention is able to kill the bacteria before the spores are able to vegetate within a body.

Dermal

A primary route of entry of bacteria such as Botulinum and Anthrax and other pathogens into the body is through skin abrasions and/or cuts, mucous membranes on the eyes, etc. The composition of the present invention alone or in an aqueous or other formulation and used as a liquid, paste or in other dermal products is effective against Anthrax and/or other pathogens that may enter man or other animals by the dermal route.

The principle involved in the above example can be utilized for control and/or eradication of pathogens in both plants and animals using the product and/or other products discussed in this patent disclosure.

The composition of the present invention is also effective in eradicating and/or disinfection of numerous types of bacterium. Experiments performed on citrus canker using the composition of the present invention will be discussed hereinafter to illustrate its efficacy against viruses, bacterium, fungus and other pathogens. Standard methods of application for citrus canker include, but are not limited to treatment of the plants with copper sulfate pentahydrate, such as that produced by the Magn Bon Corporation, (product) and a combination of the product plus a silver product for treatment of the "articles" (equipment, persons, crating, etc. containing citrus fruit) and a combination of the product plus a gold product for treatment of the "articles" (equipment, persons, crating, etc. containing citrus fruit) entering and leaving the infested area and treatment of the citrus fruit after harvest. The composition of the present invention does not cause phytotoxicity at rates effective in virtually eliminating (eradicating) the Xanthomonas bacterial disease from the plants or fruits. The product does not attack rubber, soft plastics or corrode exposed metals as other products used for the same purpose do now. The product is environmentally acceptable and non-toxic to humans and other animals.

Work done with the composition of the instant invention showed that a preferred ratio of copper:silver is 9:1 for use against citrus canker. However, any ratio within the range of ratios from 1:1 to 32:1 copper:silver is efficacious against not only citrus canker but all other pathogens mentioned herein. In order to obtain the desired 9:1 ratio or variable ratios thereof according to the method of forming the composition of the present invention two ingots are cast at the present time.

When preparing the composition containing a combination of copper, silver and/or gold, the first step is to select two (2) ingots, each of which is to have a composition based upon the desired ratio of copper:silver/gold. When preparing a composition having a 9:1 copper:silver ratio, two ingots having a composition of 90% copper and 10% silver are selected. Alternatively, gold may be used in place of or in addition to silver in similar ratios. When preparing the composition having a different ratio, appropriate amounts of copper, silver and gold are used. The two ingots are then placed in a special chamber and wires are attached to a direct current source thereby making one ingot a positive electrode and the other a negative electrode. These electrodes are then placed in a second special chamber containing water, to which an electro conductive media has been added. The water including the electro conductive media is pumped past the electrodes. As the positive ions move from the positive to the negative, and negative ions move from the negative to the positive, the resulting copper/silver ions are swept away by the water and remain in solution.

Presently it is known that after a period of approximately 3½–4 hours for 1000 gallons if the total dissolved solid (TDS) is correct for the amount of water, as the water in the second chamber is recycled over and over past the recycled electrified ingots, the water will reach the desired ratio. Once the desired copper/silver ratio is reached according to specifications, removal of any of the resulting copper/silver product from the electrified chamber normally requires additional time to "recharge" the water to its original concentration of copper/silver/gold. This timely and costly method is presently used in cooling towers, swimming pools, hot water systems, etc. The method of forming the composition of the present invention obviates the above drawbacks.

By way of example, consider a pool contains 60,000 gallons of water, and has been treated as described above using the above discussed ingots having a composition of 90% copper and 10% silver, until the water, when tested, contains 1 ppm of copper and 100 ppb of silver. After the water is heated so as to evaporate 59,999 gallons of the water, the resulting 1 gallon of water will contain 9 ounces of copper metal and 1 ounce of silver metal.

This concentration of copper to silver can then be diluted to obtain any desired ppm of copper/silver. If one pours one gallon of the concentrate, 9 ounces Cu and 1 ounce Ag, into 59,999 gallons of water, the resulting mix would be 1 ppm copper and 100 ppb silver. If the 1 gallon of concentrate is then placed in 999 gallons of water, the diluted product when tested, would reveal a 9:1 ratio of copper/silver that is 60 ppm copper and 600 ppb silver.

This method of producing the composition obtains the desired concentration. However, this process is costly and time consuming. Alternatively, the present invention provides for overcoming these drawbacks by way of a method which results in the manufacture of an effective antimicrobial composition without heat, but by a chemically reactive method.

An exemplary composition for making one gallon of concentrate involves preparing a mix, under agitation, of the following ingredients:

103 ounces of water (H2O);
14 ounces Sorbertrol ($H_2SO_4+(NH_3)_2SO_4$);
1 ounce of Tetrasilvertetraoxide ($Ag4O4$);
2 pounds of Copper Sulfate ($CuSO4H2O$), in that order.

The amounts of Tetrasilvertetraoxide and Copper Sulfate listed above produce a composition containing a 9:1 ratio of copper:silver. Alternatively, any amounts of copper to silver may be used which would produce ratios of copper:silver from between 32:1 to 1:1. in addition amounts of silver may be replaced or supplemented with gold to produce a ratio of copper:silver/gold of anywhere between 32:1 to 1:1.

When one gallon of concentrate composition, manufactured as described above, was diluted to 60 ppm copper and 600 ppb silver, and tested against XANTHOMONAS AXONOPODIS, a surrogate of citrus canker, the harmful bacteria was 99.9999% killed in thirty (30) seconds.

The composition is safe and benign to humans and animals when diluted to a 1:1000 ratio. When the diluted composition is concentrated for use, the ratio of copper to silver and/or gold always returns to the desired ratio. The composition has a major deliterious effect on garden, row, field and tree crop microbes as well as use as an antimicrobial, including but not limited to those as defined by the U.S. Environmental Protection Agency, with such uses as a hard surface disinfectant and other uses such as water purification.

It will be understood that each of the elements described above, or two or more together may also find a usefull application in other types of methods differing from the type described above.

Since the invention is described with reference to a preferred embodiment and pointed out in the annexed claims, and since numerous modifications and changes may become readily apparent to those skilled in the art after reading this disclosure, it should be understood that we do not wish to limit the scope of the overall invention to the exact composition, or method of making same, described above and claimed below, since it will be understood that various omissions, modifications, substitutions and changes in the forms and details of the invention and in its application can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A method of producing an antibacterial composition for eradicating and/or controlling pathogens comprising the steps of:

adding the ingredients of water; a compound having the chemical formula $H_2SO_4$+$(NH_3)_2SO_4$; and at least one of copper, silver and gold into a mixture;

agitating said mixture until the ingredients are blended together;

diluting said mixture to an effective antibacterial composition; and treating food products with the composition by at least one of coating, washing, spraying, rinsing, dipping, soaking and combining with the food products.

2. The method of claim 1, further comprising the step of adding inert ingredients for adjusting a pH of said composition.

3. The method of claim 2, wherein the step of adding inert ingredients includes adding at least one of surfactants, detergents and buffers.

4. The method of claim 1, wherein the at least one of copper, silver and gold is provided in a copper: silver/gold ratio of between 1:1 and 32:1.

5. The method of claim 1, wherein the at least one of copper, silver and gold is able to remain in suspended in the water.

6. The method of claim 1, further comprising the step of forming the composition in one of an aerosolized, misted, vaporized, fogged, humidified forms to produce micronized particles which are able to remain in suspension in the air for long periods of time in order to act on and eradicate or disinfect air-borne fungal spores and/or other pathogens.

7. The method of claim 1, further comprising the step of forming the composition in one of a liquid, soap, salve or other form able to be applied to a surface affected by a pathogen.

8. The method of claim 1, wherein said step of treating food products includes treating at least one of fish, shellfish, meat, milk, poultry, eggs and irrigated crops in the composition and eliminating any bacteria on or within the food product in order to minimize pathogens resulting from ingestion of the food product and increase the shelf life of the food product.

9. The method of claim 1, further comprising the step of adding the composition to a supply of liquid thereby eradicating or disinfecting pathogens from within the liquid.

10. A method of producing an antibacterial composition for eradicating and/or controlling pathogens comprising the steps of:

adding the ingredients of water; a compound having the chemical formula $H_2SO_4+(NH_3)_2SO_4$; and at least one of silver and gold into a mixture;

agitating said mixture until the ingredients are blended together; and diluting said mixture to an effective antibacterial composition.

* * * * *